(12) United States Patent
Tung

(10) Patent No.: US 9,320,692 B2
(45) Date of Patent: Apr. 26, 2016

(54) TOOTH FLUORIDATING AND REMINERALIZING COMPOSITIONS AND METHODS, BASED ON NANOAGGREGATE FORMATION

(75) Inventor: Ming S. Tung, Gaithersburg, MD (US)

(73) Assignee: ADA FOUNDATION, Chicago, IL (US)

( * ) Notice: Subject to any disclaimer, the term of this patent is extended or adjusted under 35 U.S.C. 154(b) by 0 days.

(21) Appl. No.: 12/126,426

(22) Filed: May 23, 2008

(65) Prior Publication Data

US 2008/0292565 A1    Nov. 27, 2008

Related U.S. Application Data

(60) Provisional application No. 60/939,928, filed on May 24, 2007.

(51) Int. Cl.
| | |
|---|---|
| *A61K 8/24* | (2006.01) |
| *A61K 8/19* | (2006.01) |
| *A61K 8/20* | (2006.01) |
| *A61K 8/22* | (2006.01) |
| *A61Q 11/00* | (2006.01) |
| *A61Q 17/00* | (2006.01) |

(52) U.S. Cl.
CPC ... *A61K 8/24* (2013.01); *A61K 8/19* (2013.01); *A61K 8/20* (2013.01); *A61K 8/22* (2013.01); *A61Q 11/00* (2013.01); *A61Q 17/005* (2013.01)

(58) Field of Classification Search
USPC .......................................................... 424/49
See application file for complete search history.

(56) References Cited

U.S. PATENT DOCUMENTS

| | | | | |
|---|---|---|---|---|
| 4,198,394 | A | * | 4/1980 | Faunce .............................. 424/52 |
| 4,839,156 | A | * | 6/1989 | Ng et al. ........................... 424/53 |
| 5,130,124 | A | * | 7/1992 | Merianos et al. ................ 424/53 |
| 5,508,342 | A | | 4/1996 | Antonucci |
| 5,614,175 | A | * | 3/1997 | Winston et al. .................. 424/52 |
| 5,820,852 | A | * | 10/1998 | Burgess et al. .................. 424/52 |
| 5,858,333 | A | * | 1/1999 | Winston et al. .................. 424/57 |
| 5,993,786 | A | | 11/1999 | Chow |
| 6,000,341 | A | | 12/1999 | Tung |
| 6,056,930 | A | * | 5/2000 | Tung .............................. 423/305 |
| 6,649,669 | B2 | | 11/2003 | Dickens |
| 2003/0165440 | A1 | * | 9/2003 | Roth et al. ....................... 424/50 |
| 2004/0047814 | A1 | * | 3/2004 | Xu et al. .......................... 424/49 |
| 2005/0281759 | A1 | | 12/2005 | Tung |
| 2006/0024248 | A1 | | 2/2006 | Spengler et al. |
| 2006/0110340 | A1 | | 5/2006 | Tung |
| 2006/0292090 | A1 | * | 12/2006 | Sharma et al. ................... 424/53 |
| 2007/0039519 | A1 | | 2/2007 | Kangas et al. |

FOREIGN PATENT DOCUMENTS

| | | | |
|---|---|---|---|
| WO | WO-94-04460 | * | 3/1994 |
| WO | WO-2006-006998 | * | 1/2006 |

OTHER PUBLICATIONS

WTEC.org, Nanoparticle Synthesis Strategies, 1999, www.wtec.org, p. 1-4.*
Kalita et al., Nanocrystalline calcium phosphate ceraics in biomedical engineering, Materials Science and Engineering C, 2007, 27, p. 441-449.*
Schumb, Stability of concentrated hydrogen peroxide solutions, Industrial and Engineering Chemistry, 1949, 41(5), pp. 992-1003.*
Tung et al., Remineralization by fluoride enhanced with calcium phosphates, Journal of Clinical Dentistry, 1999, 10(Special 1), pp. 1-6.*
PCT Notification of Transmittal of the International Search Report and the Written Opinion of the International Searching Authority (PCT/US 08/64707, filed May 23, 2008).
Schemehorn et al.; (2011) "Comparison of Fluoride Uptake into Tooth Enamel from Two Fluoride Varnishes Containing Different Calcium Phosphate Sources"; Source: J Clin. Dent., No. 22, pp. 51-54.
Kentucky Ecuador Partners News, dated Feb. 14, 2011; entitled: "Sealant Project—part I".
Kentucky Ecuador Partners News, dated Mar. 21, 2009; entitled: "Making a Difference: In Clark County, Kentucky and Ecuador".
(Sep. 6, 2011) "Dental health key to curbing other costly Illnesses"; available at: http://www.kentucky.com/2011/09/06/1870825/dental-health-key-to-curbing-other.html.

* cited by examiner

*Primary Examiner* — Frederick Krass
*Assistant Examiner* — Celeste A Roney

(57) ABSTRACT

Compositions and methods for forming, in an aqueous environment, a nanoaggregate of calcium fluoride and amorphous calcium phosphate-containing compound, such as amorphous calcium phosphate fluoride or amorphous calcium carbonate phosphate fluoride are described. The nanoaggregate (or nanocomposite) can release calcium, phosphate, and fluoride, and ultimately convert to the tooth mineral, fluorapatite. One method for forming such a nanoaggregate involves applying a non-aqueous (e.g., varnish-based) composition (e.g., a suspension), containing solid particles of water soluble salts of calcium, phosphate, and fluoride, to the aqueous environment of the mouth. This results in rapid solubilization of the salts, precipitation of the nanoaggregate, and tooth remineralization. Tooth fluoridation and remineralization may also be carried out by applying to the tooth a non-aqueous carrier containing the nanoaggregate. Whitening agents can also be added to these compositions and methods.

13 Claims, 3 Drawing Sheets

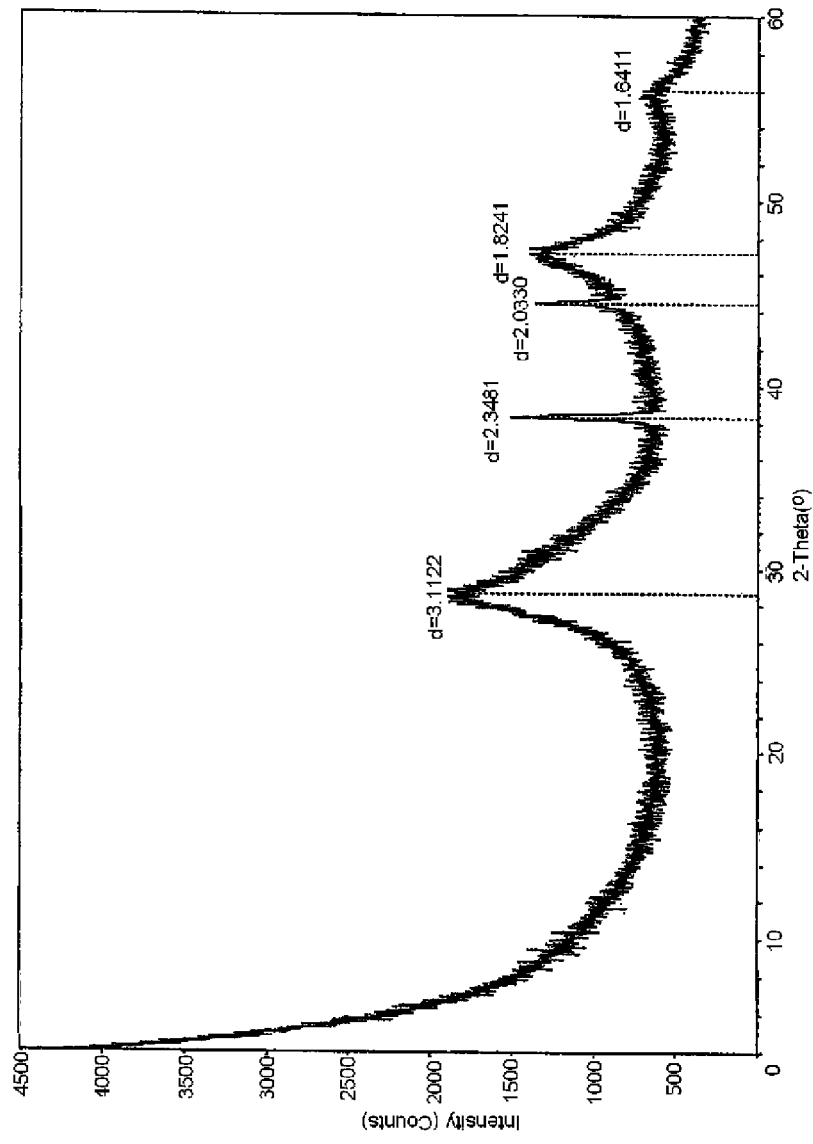
FIGURE 1 X-ray Powder Diffraction Pattern of nanoaggregate prepared by EXAMPLE 1

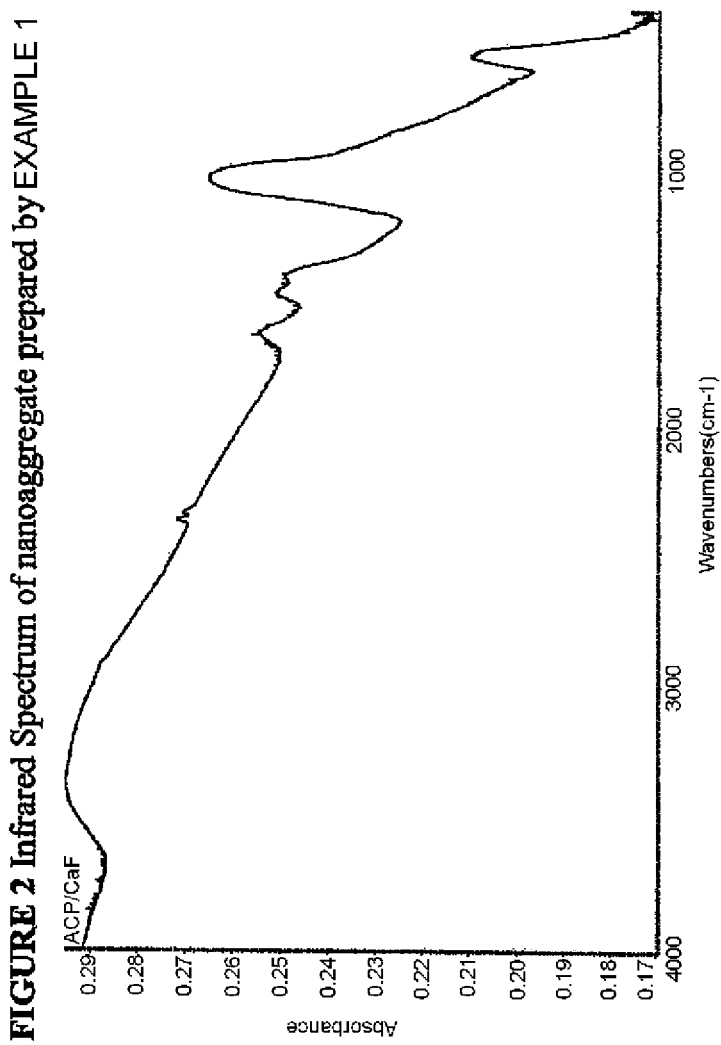

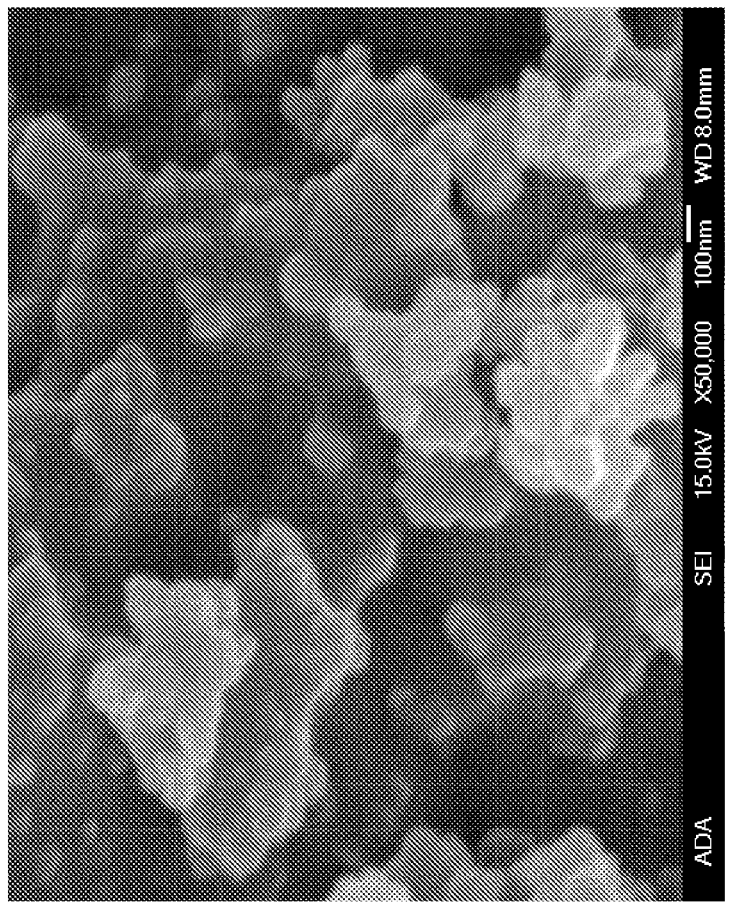
FIGURE 3 Nanoaggregate prepared by EXAMPLE 1 as observed by Scanning Electron Microscopy

TOOTH FLUORIDATING AND REMINERALIZING COMPOSITIONS AND METHODS, BASED ON NANOAGGREGATE FORMATION

FIELD OF THE INVENTION

The present invention relates to compositions and methods for forming, in an aqueous environment, a nanoaggregate of calcium fluoride and an amorphous calcium phosphate-containing compound. The formed nanoaggregate can thereafter convert to the tooth mineral, fluorapatite. Various compositions and methods for delivering the nanoaggregate are possible, including the use of suspensions of water-soluble calcium, phosphate, and fluoride salts or previously prepared nanoaggregates in non-aqueous carriers.

BACKGROUND OF THE INVENTION

A tooth is comprised of an outer hard enamel protective layer surrounding an inner dentin layer. The outer enamel layer is composed of apatite mineral crystals that are somewhat porous. Plaques, which can contain 250 or more separate microbial species, are a major cause of dental decay. These plaques use sugars and other fermentable carbohydrates to produce acids, which cause demineralization of the tooth surface. In its initial stages, a carious lesion is not readily apparent. However, with prolonged and repeated demineralization by plaque-created acids, a cavity will ultimately form at the lesion site.

When a lesion or cavity develops on the surface of a tooth, a dentist traditionally fills it, in order to prevent further spread of the decay. However, this procedure does not restore the tooth to its original state. Thus, a considerable amount of research has been directed toward the remineralization of dental lesions, with the primary objective being the deposition and/or formation of tooth mineral lost through decay. Through remineralization (e.g., with hydroxyapatite, optionally containing other ingredients such as fluoride), the tooth is not merely repaired, but restored to its original form.

Various approaches to remineralization and topical fluoridation are described, for example, in the background of U.S. Pat. No. 6,000,341 and related patents and patent applications. The '341 patent itself teaches the use of amorphous calcium phosphate compounds, such as amorphous calcium phosphate (ACP), amorphous calcium carbonate phosphate (ACCP), amorphous calcium phosphate fluoride (ACPF), and amorphous calcium carbonate phosphate fluoride (ACCPF) for use in remineralizing teeth.

Other routes for achieving tooth remineralization are described in U.S. Patent Application Publication No. 2006/0110340, where, for example, separate compositions comprising one or more soluble calcium, orthophosphate, and peroxide salts may be stabilized for storage and then activated upon use. Also, U.S. Patent Application Publication No. 2005/0281759 describes the synthesis and use of calcium peroxyphosphate compounds, in dental compositions for whitening, mineralizing, and/or fluoridating teeth.

There is an ongoing need in the art for compositions that can remineralize teeth by filling voids associated with tooth decay, mechanical injury, or even organic stain removal. The potential for dental remineralization as an alternative to conventional treatment methods is vast, since dentists currently fill millions of cavities each year. If these cavities were remineralized rather than filled, the general dental health of the public would improve. This is apparent because remineralization, unlike traditional cavity filling, effectively results in a whole tooth.

Nanoparticles have recently become a topic of considerable scientific interest, as they represent a "bridge" between bulk materials and molecular or atomic structures. While bulk materials of standard dimensions have constant physical properties regardless of size, this relationship often breaks down on the nano-scale, as surface effects become more pronounced. Eventually, for particulates having dimensions on the atomic scale, these surface effects will dominate, often with unpredictable results. For example, conventionally sized copper wire bends easily because of the movement of bulk copper atoms/clusters. In contrast, copper nanoparticles are extremely hard materials that do not exhibit the same malleability and ductility. Other properties, such as particulate solvent interactions, diffusion, agglomeration, and even color, may vary considerably in the case of nanoparticles, relative to their respective bulk materials.

The use of nanotechnology in the treatment and prevention of diseases holds great promise. However, many practical considerations associated with medical and dental applications are relevant, including biocompatibility, toxicity, and functionality under physiological conditions. While calcium, phosphate and fluoride salts have been used for tooth remineralization, previous compositions and methods utilizing these components do not form or involve the use of nanoaggregates.

SUMMARY OF THE INVENTION

The present invention is associated with the discovery of compositions which can form, nanoaggregates (or nanocomposites) of at least two components, namely, nano calcium fluoride and nano amorphous calcium phosphate-containing compounds (e.g., amorphous calcium carbonate phosphate fluoride or amorphous calcium phosphate fluoride). Without being bound by theory, the close interactions between nanoparticles of these components provide important benefits related to both tooth fluoridation and remineralization, which are each associated with the ability to readily form fluorapatite or tooth mineral. These nanoaggregates can additionally function to provide (1) both "tooth-bound" and "loose-bound" sources of fluoride (e.g., calcium phosphate fluoride and calcium fluoride, respectively) as well as (2) overall greater amounts of beneficial fluoride and calcium phosphate (which ultimately become tooth mineral) than conventional tooth fluoridation and/or remineralization compositions alone. Compositions that form such nanoaggregates, as well as the resulting nanoaggregate itself, can further contain an antimicrobial agent, such as chlorhexidine, optionally in one or more of its salt forms (e.g., chlorhexidine gluconate or chlorhexine diacetate). Other agents which may be present in these compositions include peroxides (e.g., carbamide peroxide) for tooth whitening, stain removal, and/or antimicrobial activity. Thus, the compositions and methods described herein are effective for both tooth fluoridation and remineralization, and the associated prevention and/or repair of weaknesses or lesions including dental caries, exposed dentin tubules, and voids resulting from stain removal.

Aspects of the invention therefore relate to compositions for simultaneously fluoridating and remineralizing a tooth (e.g., with final product of fluorapatite). The compositions comprise a calcium salt, a phosphate salt, and a fluoride salt, each of which is water soluble and suspended in a non-aqueous carrier. In these compositions, the three salts are in the proper ratios and concentrations, are under the proper conditions of solid/solution solubility equilibrium, have particle sizes which result in the proper dissolution kinetics, etc., such that, when in contact with the aqueous oral environment, calcium, phosphate, and fluoride ions are released, precipitate, and form a nanoaggregate of calcium fluoride and one or more amorphous calcium phosphate-containing compounds (e.g., ACPF). Representative water-soluble calcium salts include calcium sulfate, calcium oxide, calcium chloride, calcium nitrate, calcium acetate, calcium lactate, calcium peroxide, calcium glycerophosphate, and mixtures thereof. Representative water-soluble phosphate salts include sodium phosphates, potassium phosphates, ammonium phosphates, calcium phosphates, and peroxyphosphates. Representative water-soluble fluoride salts include sodium fluoride, potassium fluoride, ammonium fluoride, sodium fluorosilicate, and sodium monofluorophosphate. It will therefore be appreciated that, while in many cases three separate compounds provide the requisite sources of calcium, phosphate, and fluoride, it is also possible (e.g., in the case of a calcium phosphate-containing compound such as calcium orthophosphate) for a single compound to serve as two or even all three of the soluble calcium salt, soluble phosphate salt, and soluble fluoride salt. In compositions comprising these soluble salts, fluoride and calcium are generally present in an F/Ca molar ratio of greater than 0.4, or greater than 0.5, and typically from about 0.5 to about 5.0. However, nanoaggregate formation may occur using compositions having a broad range of F/Ca molar ratios, under the proper conditions (e.g., in an environment which promotes the proper precipitation kinetics). For example, precipitation of the nanoaggregrate is generally the result of obtaining a solution which is supersaturated with respect to both calcium fluoride and an amorphous calcium phosphate-containing compound such as amorphous calcium phosphate fluoride (ACPF).

Examples of non-aqueous carriers used to suspend particles of the calcium, phosphate, and fluoride salts include liquids such as varnishes (e.g., rosin-based), oils (e.g., a vegetable oil, a mineral oil, or an essential oil), polyols (e.g., glycerin), and alcohols. Liquid non-aqueous carriers will generally contain little water, for example, less than about 1 wt-% water. Often these compositions contain less than about 0.1 wt-% water or no water at all. Solid non-aqueous carriers include waxes, non-aqueous pastes and gels, and chewing gums. Generally, the suspended solid particles of calcium, phosphate, and fluoride salts have an average particle diameter of less than about 150 microns ($\mu$m), typically from about 1 $\mu$m to about 100 $\mu$m, and often from about 5 $\mu$m to about 100 $\mu$m. Particles having these average sizes or diameters will readily solubilize in an aqueous environment (e.g., the mouth) and form the desired nanoaggregates of calcium fluoride and an amorphous calcium phosphate-containing compound.

Other aspects of the invention relate to methods for fluoridating and remineralizing a tooth (e.g., with fluorapatite). The methods comprise combining a first aqueous solution comprising a soluble calcium salt with a second aqueous solution comprising a soluble phosphate salt and a soluble fluoride salt to obtain a nanoaggregate-delivering (or, ultimately, a fluorapatite-forming) composition. The methods further comprise, during or after preparation of the nanoaggregate-delivering composition, applying the nanoaggregate-delivering composition to the tooth. The compositions of the first and second aqueous solutions are such that, when mixed, will result in a precipitate that forms nanoaggregates of calcium fluoride and an amorphous calcium phosphate-containing compound (e.g., ACPF). The first and second aqueous solutions may be combined, for example, to obtain the nanoaggregate-forming composition prior to applying the composition to teeth, for example, by using a tray such that contact is maintained between the composition and the surface of the teeth. In the case of separate, sequential mixing and application steps, an aqueous solution comprising the nanoaggregate-forming composition described above can result prior to application. The two solutions may also be applied simultaneously or sequentially on the tooth, such that mixing and formation of the nanoaggregate occur on the tooth. The first and second aqueous solutions may together (i.e., when combined) contain fluoride and calcium in an F/Ca molar ratio as described above (i.e., generally greater than 0.4 and typically from about 0.5 to about 5.0). Often, the F/Ca molar ratio will be in the range from about 0.6 to about 5.0.

Other aspects of the invention relate to tooth remineralization compositions comprising solid particles of (a) a soluble calcium salt, (b) a soluble phosphate salt, and (c) a soluble fluoride salt. In the composition, these salts in the composition will release calcium, phosphate, and fluoride ions which precipitate and form a nanoaggregate of calcium fluoride and an amorphous calcium phosphate-containing compound (e.g., ACPF) when in contact of aqueous oral environment. In the compositions, fluoride and calcium may be present in an F/Ca molar ratio of greater than 0.5.

Other aspects of the invention relate to tooth remineralization kits comprising a first aqueous solution comprising a soluble calcium salt, and a second aqueous solution comprising a soluble phosphate salt and a soluble fluoride salt. The first and said second aqueous solutions are packaged in separate containers, and, after the solutions are combined, the resulting aqueous solution, comprising a nanoaggregate-delivery composition, may thereafter be applied to the teeth. When combined, the first and the second aqueous solutions may contain fluoride and calcium in an F/Ca molar ratio as described above.

Other aspects of the invention relate to a carbonated aqueous solution comprising a soluble calcium salt, a soluble phosphate salt, and a soluble fluoride salt. This calcium, phosphate and fluoride containing solution is stable at low pH, and precipitates a nanoaggregate of calcium fluoride and an amorphous calcium compound upon release of carbon dioxide from the solution. After application of the solution to the teeth for remineralization, the carbon dioxide is released, causing formation of the aggregate described above. The solution may contain fluoride and calcium in an F/Ca molar ratio as described above.

Other aspects of the invention relate to the nanoaggregates formed using any of the compositions and methods described above.

These and other aspects and features relating to the present invention are apparent from the following Detailed Description.

BRIEF DESCRIPTION OF THE DRAWINGS

FIG. 1 is an x-ray powder diffraction pattern of the sample of the nanoaggregate (or nanocomposite) of nano calcium fluoride and nano amorphous calcium carbonate phosphate fluoride (ACCPF) prepared in Example 1.

FIG. 2 is an infrared (IR) spectrum of the nanoaggregate prepared in Example 1.

FIG. 3 shows the Scanning Electron Microscopy (SEM) image of the nanoaggregate prepared in Example 1.

DETAILED DESCRIPTION OF THE INVENTION

Calcium and phosphate are predominant constituents of tooth mineral, and can therefore by used for tooth remineralization. Fluoride prevents dental caries (tooth decay) by inhibiting the demineralization process and/or promoting the formation of calcium phosphate mineral. Thus, fluoride, calcium, and phosphate have the ability to prevent dental caries when properly applied to the tooth. The main ingredients that ultimately convert to tooth mineral, namely calcium and phosphate, can be rapidly deposited on and in the tooth through the formation of an amorphous calcium phosphate-containing compound such as amorphous calcium phosphate fluoride (ACPF). Also, an effective approach for additionally delivering fluoride together with the ACPF involves the deposit of calcium fluoride. Thus, both "tooth-bound" fluoride (e.g., calcium phosphate fluoride) and "loose-bound" fluoride (e.g., calcium fluoride) are delivered to the tooth. The former is less soluble and remains in the mouth for a significantly long period while the latter dissolves relatively quickly and maintains a therapeutically effective fluoride concentration in the saliva (i.e., the environment surrounding the tooth) for a short time.

In view of the above considerations, methods and compositions have been developed to deposit one or more amorphous calcium phosphate-containing compounds (e.g., ACPF) and calcium fluoride simultaneously as a nanoaggregate. These new approaches achieve a synergistic effect to improve both fluoridation and remineralization. The synergistic improvements in these processes extend not only to the deposition of fluoride and amorphous calcium phosphate-containing compounds, but also to the therapeutic effects resulting from this deposition. In particular, methods and compositions having these desired characteristics are capable of delivering (1) nano calcium fluoride and (2) amorphous calcium phosphate-containing compounds (e.g., amorphous calcium phosphate fluoride) simultaneously to the tooth as a nanoaggregate (or nanocomposite) of these components. These closely packed nanoaggregates stabilize both active ingredients, control their release, and respond to the acidic environment rapidly. The calcium fluoride component of this nanoaggregate provides both a source of tooth mineral calcium as well as a source of "loose-bound" fluoride. The amorphous calcium phosphate-containing compound (e.g., ACPF), delivered to the tooth as another component of the nanoaggregate, is effectively a solid "solution" containing calcium, phosphate ions, and fluoride ions (e.g., in the case of an amorphous calcium phosphate fluoride). This solid solution of calcium and phosphate ions has no long range structure but is nevertheless homogeneous on an angstrom scale. The composition of this component, namely the amorphous calcium phosphate-containing compound, may vary. Under physiological conditions, this compound has a high solubility and can also readily convert to apatite, which allows remineralization to proceed at a practical rate for therapeutic purposes. Such amorphous calcium phosphate-containing compounds include amorphous calcium phosphate (ACP), amorphous calcium phosphate fluoride (ACPF), amorphous calcium carbonate phosphate (ACCP), amorphous calcium carbonate phosphate fluoride (ACCPF), and mixtures of two or more of these in any mixing ratio. The description of these compounds in U.S. Pat. No. 6,000,341 is incorporated by reference.

The formation of an amorphous calcium phosphate-containing compound, as a component of the nanoaggregate, is also beneficial in that this compound is more soluble under acidic conditions, and thus releases more calcium, phosphate, and fluoride ions when the tooth is "under attack" or most susceptible to demineralization. Moreover, dissolution of this compound neutralizes acidic conditions in the mouth and raises oral pH to values less conducive to demineralization (i.e., more favorable to remineralization). The fluoride ions released from calcium fluoride and also from the amorphous calcium phosphate-containing compound (e.g., ACPF and/or ACCPF) are beneficially deposited on the tooth as fluoroapatite. In this manner, the nanoaggregate can simultaneously deliver all the necessary and desirable components for tooth remineralization and fluoridation, as discussed above. Preferably, sufficient fluoride is available in compositions of the present invention for the formation of ACPF as the amorphous calcium phosphate-containing compound.

Thus, without being bound by theory, the inventive dental compositions have the ability to quickly release calcium, phosphate, and fluoride in sufficient amounts and at the appropriate ratios, such that a calcium fluoride/amorphous calcium phosphate-containing nanoaggregate is formed (e.g., by precipitation). The release or formation may occur in situ (e.g., in the aqueous, oral environment) or may otherwise occur some time prior to the application of the formed nanocomposite to the tooth. In either case, the nanoaggregate (or nanocomposite) contains both nano calcium fluoride and nano amorphous calcium phosphate-containing components which act synergistically in promoting the advantageous tooth fluoridation and remineralization properties, as described above. That is, the nanoaggregate has the ability to deposit more fluoride and calcium phosphate, relative to the individual or separate use of either fluoride compositions or calcium and phosphate containing compositions. Also, the structural arrangement of the calcium, phosphate, and fluoride, as a nanoaggregate, improves therapeutic ability for treating and preventing dental caries through the ultimate formation of tooth mineral. It is believed that these advantages with respect to remineralization at least partly result from the close interactions between nanoparticles of the two nanoaggregate components, leading to the formation of fluorapatite, the most stable tooth mineral.

The nanoaggregate, having the beneficial properties discussed above, is thought to result from the "self assembly" of calcium fluoride and amorphous calcium phosphate-containing compounds (e.g., ACPF) precipitated from the calcium, phosphate, and fluoride ions, released under the proper conditions and in the proper amounts and ratios, using the compositions and methods discussed herein. This self assembly is accelerated by electrostatic interaction between positively charged calcium fluoride and negatively charged phosphate in the amorphous calcium phosphate-containing compounds, resulting in a synergistic precipitation effect. This particular structure is advantageous with respect to both the amounts of calcium, phosphate, and fluoride available for remineralization, as well as the effectiveness of these ions in generating tooth mineral. Thus, through the formation and (simultaneous or subsequent) delivery of a nanoaggregate using the compositions and methods described herein, the effectiveness of fluoride in treating and preventing caries is enhanced by the presence of calcium and phosphate. Likewise, the effectiveness of the calcium and phosphate ions to form the most stable tooth mineral, fluorapatite, is enhanced by the presence of fluoride.

Several types of systems (i.e., nanoaggregate-delivering compositions, also referred to herein as nanoaggregate-forming compositions) have the potential to form the desired, multifunctional, therapeutic nanoaggregate of calcium fluoride and an amorphous calcium phosphate-containing compound. For example, a stable, single phase non-aqueous medium or carrier may be used to suspend (or mix with) solid particles of a calcium salt, a phosphate salt, and a fluoride salt, with each of these salts being water-soluble. Upon application of this composition to the tooth (i.e., in the aqueous environment of the mouth), the salts dissolve readily in sufficient concentrations causing the resulting saliva-containing solution to become supersaturated with respect to calcium fluoride and one or more amorphous calcium phosphate-containing compounds. The supersaturated solution (of saliva) then rapidly precipitates and forms the nanoaggregate as described above.

Suitable non-aqueous carriers for use in this application include liquids, pastes, and gels (e.g., tooth varnishes, dental resins, dental adhesives, dental composites, pit and fissure sealants). Other suitable non-aqueous media or carriers include oils (e.g., vegetable oils, mineral oils, and essential oils), waxes, esters, alcohols, and polyols. Essential oils have antiseptic and antimicrobial effects, and include thymol, menthol, eucalyptol, and eugenol. Other non-aqueous media or carriers, as discussed above, are varnishes, which typically comprise a natural polymer (e.g., a rosin such as colophony or a pine resin-based material) or synthetic polymer (e.g., a polyurethane based resin or a polymethacrylate based resin such as polymethyl methacrylate) in alcoholic solution. Other non-aqueous carriers can include reactive monomer systems (e.g., in the form of a paste with suitable fillers) that cure or polymerize in the presence of radiation (e.g., UV light) or moisture. Reactive monomer systems thus include one-part systems that can be cured, as well as two-part resin systems that cure via chemical reaction, upon combining the two parts. Such reactive monomer systems which are useful for oral applications are known in the art and described, for example, in U.S. Pat. Nos. 5,508,342 and 6,649,669, the description of these monomer systems being incorporated by reference. Varnishes have been used for sustained-release tooth fluoridation and are also applicable as carriers in the nanoaggregate-delivering compositions described herein. Tooth varnishes are generally compounds that are topically applied to teeth with a special brush, cotton, or tray and harden over a short time by contact with saliva, air, or both.

Solid materials (e.g., dental flosses, floss waxes, confections, chewing gums, and polymeric matrices) as described in U.S. Pat. No. 5,993,786 may also function similarly as carriers to provide the calcium, phosphate, and fluoride ingredients in sufficient quantities and ratios to cause nanoaggregate formation in the aqueous environment of the mouth. Suitable polymers which may be used in a solid polymeric matrix carrier are described, for example, in U.S. Pat. No. 5,508,342, the description of the disclosed polymeric carriers being incorporated by reference. Chewing gum compositions as non-aqueous media include natural or synthetic gum base materials, such as natural tree resins and latexes, as well as synthetic polymers. Examples include chicle and other polyterpenes and isoprenes, styrenes, butadienes, poly(vinyl acetate), or polyethylene.

Any of these non-aqueous carriers may contain minor quantities of water but are generally essentially or completely free of water (e.g., contain less than 1 wt-% water, less than 1000 ppm water, or less than 100 ppm water). It is also possible to provide the calcium salt, phosphate salt, and fluoride salt in a solid powder comprising solid particles of these salts without any carrier, or with an inert material (e.g., a water-soluble solid such as a starch). Because the salts are soluble in aqueous media, they will dissolve and form a nanoaggregate-delivering composition in situ (i.e., in the aqueous, oral environment). Whether solid particles of soluble calcium salt, soluble phosphate salt and soluble fluoride salt are suspended in a non-aqueous medium or used without any medium, small particle sizes will improve dissolution rate in the mouth as well as minimize any unpleasant, gritty texture. The average particle size, with respect to at least one of these salts, two of these salts, or all three of these salts, will generally be less about 150 microns ($\mu m$), typically from about 1 to about 100 $\mu m$ and often from about 5 to about 100 $\mu m$.

Another type of system for forming and delivering the desired nanoaggregate involves the use of separate, aqueous solutions. One solution can comprise a soluble calcium salt and a second solution can comprise a soluble phosphate salt and a soluble fluoride salt. This allows the calcium, phosphate, and fluoride ions to be solubilized in separate, stable environments prior to being combined in amounts and ratios which lead to the precipitation or formation of the nanoaggregate, as described above. While this delivery system is thus exemplified by the use of two aqueous solutions, one of ordinary skill having regard for the present disclosure can readily contemplate alternative delivery systems within the scope of the invention, including those with more than two (e.g., three) aqueous solutions or with aqueous solutions having varying compositions (e.g., where the soluble phosphate salt is distributed between the first and second solutions). The overriding consideration is maintaining the aqueous solutions and their respective calcium, phosphate, and fluoride ions in stable concentrations under storage conditions, such that precipitate formation is avoided, before the solutions are combined. Upon mixing or combination of the solutions, the resulting mixture has the desired properties which allow the formation and delivery of a nanoaggregate, as described above, to the tooth, thereby resulting in remineralization (e.g., through the formation of fluorapatite) and fluoridation (e.g., by maintaining the fluoride concentration in mouth). Tooth remineralization kits may therefore comprise two or more aqueous solutions that, when combined, result in the formation of a calcium fluoride/amorphous calcium phosphate-containing compound nanocomposite. The two or more aqueous solutions, containing the soluble calcium, phosphate, and fluoride ingredients, may also be effectively separated in stable concentrations, by using separate layers in an aqueous gel or polyol carrier. In this manner, for example, a soluble calcium salt can be contained in one layer of an aqueous gel and soluble phosphate and soluble fluoride salts in another aqueous layer. An aqueous gel solution, such as an aqueous polyol, can be used as a carrier for either or both (or all) of the aqueous solutions that are combined to yield the nanoaggregate-forming composition (in this case an aqueous solution). When the aqueous gel is applied to the teeth, the soluble salts are combined to form and deliver the nanoaggregate, as described above. In another representative embodiment, one of the solutions may be microencapsulated and suspended in another solution. In this case, the two solutions are mixed just before or during application.

Solutions of soluble calcium, phosphate, and fluoride salts, as described above may therefore be mixed or combined prior to the application to the tooth surface, such that the combination and application steps are performed sequentially. For example, a first aqueous solution comprising a soluble calcium salt may be first combined and mixed thoroughly in a container such as a cup or a tray, with a second aqueous solution comprising a soluble phosphate salt and a soluble fluoride salt. In this manner, the nanoaggregate is formed in an aqueous composition prior to and/or during application to the teeth. Alternatively, the compositions may be mixed on the teeth at the time of application (i.e., use) to the teeth in a simultaneous manner. Thus, simultaneous mixing and application (i.e., nanoaggregate delivery) includes methods wherein a first, calcium-containing aqueous composition is applied onto the surface of the teeth (e.g., applying a solution with a cotton tip) and a second phosphate- and fluoride-containing aqueous composition is then applied, such that it is combined with the applied first composition.

It is also possible to maintain solubilized calcium, phosphate, and fluoride salts in a single, stable aqueous composition having the desired amounts and ratios of these ions which "self assemble," as described previously, to form a nanoaggregate of two components, namely calcium fluoride and an amorphous calcium phosphate-containing compound. In this case, the precipitation or nanoaggregate formation is effected through changing one or more conditions (e.g., pH or temperature) of the aqueous composition to destabilize it, such that the solution becomes supersaturated and precipitation ensues. For example, a pH change for inducing precipitation of the nanocomposite can result from the release of carbon dioxide pressure. During storage under the pressurized carbon dioxide atmosphere, a single solution can stably maintain relatively high concentrations of calcium, phosphate, and fluoride ions at a relatively low pH. When the gas is released upon, or shortly before, application to the tooth, the aqueous solution pH rises, resulting in an unstable, supersaturated condition under which the nanoaggregate described above is readily formed. Another method for causing supersaturation with subsequent nanocomposite formation involves increasing the aqueous solution temperature from a stable and relatively lower storage temperature (e.g., refrigeration temperature) to an unstable and relatively higher use temperature, such as room temperature or body temperature (i.e., in the mouth). Thus, altering pH and/or temperature to induce instability and precipitation therefore represents an alternative method of forming the nanoaggregate, either in situ or prior to use.

Regardless of the particular method and nanoaggregate-delivering composition used (e.g., a suspension of salts in an non-aqueous carrier, a mixture of more than one aqueous solution, a single aqueous solution which has become destabilized/supersaturated, etc.), it has been found that various amounts and ratios of the calcium, phosphate, and fluoride generally lead to the effective formation of the desired, two-component nanoaggregate described above. For example, good results may be obtained with nanoaggregate-delivering compositions generally having an initial concentration of calcium (as total Ca) of greater than about 3 millimolar (mM) (e.g., from about 3 to about 500 mM), an initial concentration of phosphate (as total $PO_4$) of greater than about 5 mM (e.g., from about 5 to about 200 mM), a concentration of fluoride (as total F) of greater than about 3 ppm by weight (e.g., from about 3 to about 6000 ppm), and a pH of greater than about 6 (e.g., from about 6 to about 10). The initial concentrations refer to those achieved in oral environment when the system is applied and is dissolved, and prior to precipitation. The concentrations and the pH are such that the oral environment becomes supersaturated with respect to both calcium fluoride and an amorphous calcium phosphate-containing compound (e.g., ACPF) as the soluble salts dissolve.

Therefore, regardless of type of nanoaggregate-delivering composition or method used to obtain the composition (e.g., by combining two aqueous solutions), including the compositions and methods described herein, an important property is the ability of the nanoaggregate-forming composition to provide, in the oral environment, a solution that is supersaturated with respect to both calcium fluoride ($CaF_2$) and at least one amorphous calcium phosphate-containing compound.

Examples of aqueous nanoaggregate-delivering compositions, as discussed herein, include those resulting from combining two or more aqueous solutions or those resulting from the release of carbon dioxide pressure to effect a pH change. In such aqueous nanoaggregate-delivering compositions, the property of being supersaturated with respect to both components of the nanoaggregate (calcium fluoride and an amorphous calcium phosphate-containing compound) is readily verified by determining the calcium, fluoride, phosphate, and carbonate ion concentrations after preparation of the aqueous nanoaggregate-delivering composition (e.g., after combining aqueous solutions, releasing carbon dioxide pressure, etc.) but prior to the formation of any precipitate. The determination can be theoretical, for example, by assuming all calcium, fluoride, phosphate, and carbonate sources are solubilized into ionic species and accounted for as described below (e.g., a diphosphate species is considered to contribute two ionic phosphate groups). The property of being supersaturated with respect to either or both of the nanoaggregate components may also be analytically determined (e.g., by diluting, prior to any precipitate formation, a sample of the resulting nanoaggregate-forming composition such that it is no longer supersaturated, measuring the ion concentrations, and calculating the ion concentrations prior to dilution).

Supersaturation with respect to any component of the nanoaggregate is therefore a function of ion concentrations (e.g., the calcium ion and fluoride ion activities, $[Ca^{+2}]$ and $[F^-]$) in the resulting aqueous nanoaggregate-forming composition relative to the solubility product ($K_{sp}$) of that component, which is normally determined at 25° C. For example, in the case of $CaF_2$, the solubility product at these conditions is $3.98 \times 10^{-11}$ ($10^{-10.4}$). An aqueous solution becomes supersaturated with respect to calcium fluoride when the ionic product $[Ca^{+2}] \times [F^-]^2$ exceeds this solubility product. The degree of supersaturation (DS) of calcium fluoride may be defined as the ratio of this product ($[Ca^{+2}] \times [F^-]^2$) to the solubility product ($K_{sp}$) minus 1 (DS=$([Ca^{+2}] \times [F^-]^2/K_{sp})-1$) with a DS of greater than 0 indicating the supersaturation. Likewise, the property of supersaturation and the degree of supersaturation may be similarly determined in this manner for any amorphous calcium phosphate-containing compound, as a component of the nanoaggregate (e.g., ACP, ACPF, ACCP, or ACCPF). In the case of ACP $[Ca_3(PO_3)_2]$, the solubility product ($K_{sp}$) is $1.6 \times 10^{-25}$ ($10^{-24.8}$) and an aqueous solution becomes supersaturated with respect to ACP when the ionic product $[Ca^{+2}]^3 \times [PO^{-3}]^2$ exceeds this $K_{sp}$ value. According to one embodiment of the invention, therefore, the nanoaggregate-forming composition has $CaF_2$ and ACP ionic products exceeding both of their respective solubility products, such that the composition is supersaturated with respect to both components.

In the case of a nanoaggregate-forming composition, as described herein, in which the carrier is a non-aqueous liquid or solid, the property of supersaturation is based on an approximation of conditions in the oral environment when the non-aqueous composition is introduced and mixes thoroughly with saliva. For example, a convenient test involves vigorously mixing the non-aqueous composition (e.g., containing water-soluble calcium, phosphate, and fluoride salts) with an equal volume of de-ionized water at 25° C. and pH=7, for a specified time period (e.g., 30 seconds or 1 minute) and then evaluating the resulting aqueous phase in the manner described above, to determine whether it is supersaturated with respect to both calcium fluoride and an amorphous calcium phosphate-containing compound (i.e., with respect to at least one of, but possibly two of, three of, or all four of, the amorphous-calcium phosphate containing compounds ACP, ACPF, ACCP, and ACCPF). In another test for supersaturation, is as follows: After vigorously mixing the non-aqueous composition (e.g., containing water-soluble calcium, phosphate, and fluoride salts) with an equal volume of de-ionized water at 25° C. and pH=7, as described above, but for a longer time period (e.g., 30 minutes), the solution is filtered and any formed precipitates are analyzed (e.g., using scanning electron microscopy). The precipitation of nanoaggregate establishes that the solution is supersaturated with respect to both calcium fluoride and an amorphous calcium phosphate-containing compound.

Aqueous or non-aqueous compositions containing water soluble salts, as described herein, are normally supersaturated, according to the determination methods discussed above, with respect to both calcium fluoride and an amorphous calcium-phosphate-containing compound. Supersaturation with respect to both of these components of the nanoaggregate renders the compositions capable of forming or delivering the nanoaggregate in the oral environment. Generally, the degree of supersaturation, as defined above, is at least 1 for one or both of the components of the nanoaggregate. Degrees of supersaturation of less than 1, when determined as described above, can in some cases readily result in nanoaggregate formation due to specific conditions (pH, temperature, the presence of biological ions, etc.) existing in the oral environment.

Normally, the degree of supersaturation with respect to one or both of the components of the nanoaggregate is independently at least 1.0, at least 1.5, at least 2.0, at least 5.0, or at least 10.0. Higher degrees of supersaturation may be desirable to improve the kinetics of nanoaggregate formation and precipitation. Upper limits of the degrees of supersaturation may be 50, 100, 1000, or more.

The conditions required for the formation of the novel nanoaggregate, for example, using a composition comprising a non-aqueous carrier, include the proper pH, ion molar ratios, and dissolution equilibria and kinetics (which depend on temperature and particle size). These necessary criteria are described herein or are otherwise apparent, through routine experimentation, to one having ordinary skill in the art, with regard for the present disclosure. The presence of a nanoaggregate may be verified by known analytical techniques such as Scanning Electron Microscopy (SEM). Techniques such as X-ray Powder Diffraction (XRD) and Infrared Spectroscopy (IR) may be used to identify and characterize deposited mineral solids in terms of various features such as the extent of crystallinity.

As discussed above, an aspect of the invention is associated with the discovery that the deposition of calcium and phosphate from nanoaggregate-delivering compositions has the potential to concurrently allow the deposition and the utilization of considerably more fluoride than previously thought possible. Also, the incorporation of calcium and phosphate salts increases the release of fluoride from the nonaqueous carriers, such as varnish, since the dissolution of these salts increases the porosity of the varnish and facilitates the release of fluoride imbedded in the varnish. Thus, the compositions and methods of the present invention may effectively result in the deposition of relatively larger amounts of both loose-bound and tooth-bound fluoride for both fluoridation (e.g., through formation of calcium fluoride and one or more amorphous calcium phosphate-containing compounds (such as ACPF) and tooth remineralization (e.g., through the formation of fluorapatite). In these nanoaggregate-delivering compositions, the F/Ca molar ratio is generally greater than 0.4, and typically in the range from about 0.5 to about 5.0, often in the range from about 1.0 to about 3.5.

Mixtures of soluble calcium salts (e.g., a mixture of calcium chloride and calcium lactate), as well as mixtures of soluble phosphate salts, and/or mixtures of soluble fluoride salts may be used in the nanoaggregate-delivering compositions described herein. The amounts and moles of calcium, phosphate and fluoride, for purposes of determining concentrations and mole ratios, are therefore based on the combined contributions of Ca, $PO_4$, and F from all sources of soluble calcium salts, soluble phosphate salts, and soluble fluoride salts, respectively. Any peroxymonophosphate ($PO_5^{-3}$) and/or diperoxymonophosphate ($PO_6^{-3}$) groups in these compositions are included in the determination of the amounts and moles of phosphate. The same applies to hydrogen peroxyphosphate ($HPO_5^{-2}$), dihydrogen peroxyphosphate ($H_2PO_5^{-1}$), hydrogen diperoxyphosphate ($HPO_6^{-2}$), dihydrogen diperoxyphosphate ($H_2PO_6^{-1}$) and other phosphate groups. Disphosphates (e.g., diphosphate, peroxydiphosphate, and diperoxydiphosphate), triphosphates, and polyphosphates are also included as phosphates for purposes of these calculations, where, for example, a mole of disphosphate is considered equivalent to two moles of phosphate when determining mole ratios. A single compound (e.g., calcium peroxyphosphate or calcium monofluorophosphate), may serve as a source of two, or even all three, of the calcium, phosphate, and fluoride ingredients of the nanoaggregate-delivering compositions described herein.

The nanoaggregate-delivering compositions, or any or all of the solutions which are combined to form it (e.g., aqueous solutions comprising one or more of a soluble calcium salt, a soluble phosphate salt and a soluble fluoride salt, as described above) may also contain a tooth whitening agent such as peroxide or otherwise may be essentially or completely free of peroxide (e.g., contain less than 10 ppm of peroxide, less than 5 ppm of peroxide, or less than 1 ppm of peroxide). In the case where a single aqueous solution or a combination of aqueous solutions are used to form the nanoaggregate-delivering composition, any or all of these aqueous solutions may be essentially or completely free of non-aqueous constituents such as alcohols, ketones, non-aqueous gels, etc. (e.g., the composition may contain less than 10 ppm, less than 5 ppm, or less than 1 ppm of non-aqueous constituents). Additionally, the nanoaggregate-delivering composition, or any or all of the solutions used to form it, may contain an antimicrobial agent such as chlorhexidine.

Soluble calcium salts referred to herein include salts that either contain calcium ions or decompose when used orally to yield calcium ions. Soluble calcium salts refer to those having calcium ion solubility in water of at least about 14 mM (or at least about 560 ppm) at 25° C. and pH of 7.0. When exposed to saliva, soluble calcium salts therefore provide a source of calcium in sufficient concentration for the formation of a nanoaggregate as described herein. Soluble calcium salts include, but are not limited to, calcium sulfate (e.g., plaster of Paris), calcium chloride, calcium nitrate, calcium acetate, calcium bromide, calcium gluconate, calcium benzoate, calcium glycerophosphate, calcium formate, calcium fumarate, calcium oxide, calcium lactate, calcium butyrate, calcium isobutyrate, calcium malate, calcium propionate, and calcium valerate.

Soluble phosphate salts refer to those having a phosphate ion solubility in water of at least about 40 mM (or at least about 3800 ppm) at 25° C. and pH of 7.0, thus providing a source of phosphate sufficient for nanoaggregate formation and subsequent remineralization. Preferred soluble phosphate salts include the alkali metal, alkaline earth metal, and ammonium phosphate salts. Representative soluble phosphate salts include monosodium phosphate, disodium phosphate, trisodium phosphate, monopotassium phosphate, dipotassium phosphate, tripotassium phosphate, monoammonium phosphate, diammonium phosphate, triammonium phosphate, monocalcium phosphate monohydrate (MCMP), and monocalcium phosphate anhydrate (MCPA). Other phosphate salts are the more highly oxidized peroxyphosphates, which include peroxymonophosphates ($PO_5^{-3}$) and diperoxymonophosphates ($PO_6^{-3}$) such as the alkali metal, alkaline earth metal, and ammonium salts of peroxymonophosphate and diperoxymonophosphate. Representative Peroxymonophosphate salts include monopotassium peroxymonophosphate, dipotassium peroxymonophosphate, tripotassium peroxymonophosphate, monosodium peroxymonophosphate, disodium peroxymonophosphate, trisodium peroxymonophosphate, monoammonium peroxymonophosphate, diammonium peroxymonophosphate, and triammonium peroxymonophosphate and calcium peroxymonophosphates. Representative Diperoxymonophosphate salts include monopotassium diperoxymonophosphate, dipotassium diperoxymonophosphate, tripotassium diperoxymonophosphate, monosodium diperoxymonophosphate, disodium diperoxymonophosphate, trisodium diperoxymonophosphate, monoammonium diperoxymonophosphate, diammonium diperoxymonophosphate, and triammonium diperoxymonophosphate.

Soluble fluoride salts refer to those having a fluoride ion solubility in water of at least about 1000 ppm at 25° C. and pH of 7.0, thus providing a source of source of fluoride sufficient for formation of nano calcium fluoride, as a component of the nanoaggregate, as well as possibly the formation of nano amorphous calcium phosphate fluoride, as another component. Representative soluble fluoride salts include sodium fluoride, potassium fluoride, zinc fluoride, stannous fluoride, zinc ammonium fluoride, sodium monofluorophosphate, sodium hexafluorosilicate, potassium monofluorophosphate, laurylamine hydrofluoride, diethylaminoethyloctoylamide hydrofluoride, 1-ethanol-2-hexadecylimidazoline dihydrofluoride, dodecyltriethylammonium fluoride, tetraethylammonium fluoride, didecyldimethylammonium fluoride, cetylpyridinium fluoride, dilaurylmorpholinium fluoride, N-carboxymethyl-N-dodecyldiethylammonium fluoride, sarcosine stannous fluoride, glycine potassium fluoride, glycine hydrofluoride, and sodium monofluorophosphate.

The nanoaggregate-delivering compositions may contain one or more conventional additives such as surfactants (e.g., anionic, cationic, nonionic, and zwitterionic surfactants), cosurfactants or cleansing agents, soaps, flavoring agents, sweetening agents (e.g., xylitol, licorice extract), aroma agents, astringents, anti-plaque agents, anti-calculus agents, anti-bacterial agents (e.g., cetyl pyridinium chloride, triclosan, or chlorhexidine), additional preservatives and/or stabilizers, sudsing agents, humectants, thickening agents (including inorganic thickeners such as hydrated silica), binding agents or cothickeners, coloring agents, abrasive polishing agents, buffering agents, alkali metal halide salts, desensitizing agents, healing agents, other preventative caries agents, vitamins, amino acids, proteins, opacifiers, antibiotics, antienzymes, enzymes, oxidizing/whitening agents, antioxidants, chelating agents, etc. When used, these additives are present in amounts that do not substantially adversely affect the desired nanoaggregate-delivering capabilities of the composition, as discussed above.

Examples of oxidizing and whitening agents which are beneficially present in the nanoaggregate-delivering compositions include peroxides and hexametaphosphates. If peroxide is used, it may be initially stabilized for storage by maintaining it at an acidic pH in a stabilized aqueous peroxide solution, optionally containing the soluble phosphate salt and/or the soluble fluoride salt. The stabilized aqueous peroxide solution may then become destabilized, or reactive for tooth whitening upon use, by increasing pH and/or removing phosphate. Destabilization of peroxide in this manner results in the formation of perhydroxyl anions/radicals, which are beneficial for stain removal and whitening.

Associated with these findings is the provision of tooth whitening and remineralization kits comprising two or more compositions, and methods of using such kits. The first composition is a calcium-containing composition in the form of a first aqueous solution comprising a soluble calcium salt and the second composition is a stabilized peroxide composition in the form of a second aqueous solution comprising both a soluble peroxide salt and a soluble phosphate salt. Preferably, the first and second compositions have an alkaline pH and an acidic pH, respectively. In the mixture that results from combining these compositions, the peroxide becomes activated by the presence of calcium ion, which causes (i) the precipitation of an amorphous calcium phosphate-containing compound and consequently (ii) the loss of stabilizing phosphate ion. Moreover, the increase in pH of the second composition, resulting from combining the solutions, provides an optional, second mechanism to activate the peroxide. In an alternate embodiment, a third, aqueous pH-control solution, preferably having an alkaline pH, is used to increase the pH of the soluble peroxide in the second aqueous solution and thereby activate it, prior to or during application to the teeth.

Preferably, the aqueous solution comprising the stabilized, soluble peroxide and the aqueous pH-control solution combine to yield a mixture having a pH from about 5 to about 9, which is generally tolerable in terms of taste. Preferably, the peroxide is activated using both of the above-described approaches of removing stabilizing phosphate ion through precipitation and increasing pH. Additionally, either or both of these peroxide activation methods may be combined with the use of a catalytic agent to further enhance peroxide destabilization. In particular, catalytic agents such as metal ions are suitable to facilitate the break down of peroxide and consequently the formation of perhydroxyl anions/radicals.

A number of agents, if initially present in the aqueous solution comprising the soluble calcium salt (or other composition that is initially maintained separate from a stabilized peroxide composition), can actively catalyze the break down of peroxide. These include catalytic ions, such as metal ions, including manganese, iron, chromium, cobalt, nickel, copper, zinc, and barium. Other catalytic ions including halide anions such as chloride, bromide, and iodide are also useful for this purpose, as well as selenium. Combinations of agents may also be employed. In a preferred embodiment, therefore, the aqueous solution comprising the soluble calcium salt (i.e., the source of calcium ions) comprises an agent that catalyzes the break down of peroxide. Preferably, the agent is a catalytic ion. More preferably, the agent comprises manganese and, even more preferably, comprises a combination of manganese and zinc. Zinc exhibits an unusual capacity to either stabilize, or catalyze the break down of, hydrogen peroxide. For any of these catalytic agents, high concentrations are not required to achieve a significant increase in the rate of peroxide breakdown. In general, therefore, any of these catalysts will be effective at a concentration of 100 ppm or less, and, if used, are preferably present, when combined with peroxide, at a concentration from about 1 to about 100 ppm.

Thus, the catalytic agent may optionally be present in the a first aqueous solution comprising the soluble calcium salt which is combined with a second aqueous solution comprising the soluble peroxide salt and optionally further comprising the soluble phosphate salt and soluble fluoride salt. It is therefore possible, in view of this description, to activate peroxide by one, two, or all three mechanisms (e.g., by contact with an aqueous solution comprising a soluble calcium salt) upon use, or shortly prior to use, namely: (1) the removal of the stabilizing phosphate, (2) increasing pH and/or (3) the use of one or more catalytic agents. The nanoaggregate-delivering composition may be in any conventional form, such as a paste, polish, abrasive slurry, gel, self-adhesive strip, cream, mouthwash, rinse, spray, cleanser, floss, cream, a floss wax, chewing gum, lozenge, tablet, powder, pumice flour, carbonated solution, edible food product, confection, reactive monomer system, polymeric matrix, etc.

In view of the present disclosure, one or ordinary skill in the art can adjust (1) the amounts and types of calcium, phosphate, and fluoride salts as well as (2) the particle sizes of the solid calcium, phosphate, and fluoride salts (in cases, such as with non-aqueous carriers, where solid particles are used), and, if necessary, the solution pH values, according to the particular carrier and the desired nanoaggregate formation rate, which in turn effects tooth remineralization. Overall, aspects of the invention are directed to the exploitation of the unique properties of nanostructures to not only achieve, but also enhance, dental therapy based on simultaneous tooth remineralization and fluoridation. Other beneficial agents, such as those having antimicrobial and/or whitening properties, may be incorporated into nanoaggregate-forming compositions, as described herein, or into the resulting nanoaggregate itself.

For purposes of this disclosure, concentrations which are expressed in "ppm," "wt-%," or simply "%" are all based on weight. Therefore, a solution containing 1000 ppm of a salt will contain 1 gram of that salt per kg of solution.

Throughout this disclosure, various aspects are presented in a range format. The description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual whole and fractional numbers within that range, for example, 1, 2, 2.6, 3, 4, 5, and 6. This applies regardless of the breadth of the range.

In view of the above, it will be seen that several advantages may be achieved and other advantageous results may be obtained. As various changes could be made in the above compositions and methods without departing from the scope of the present disclosure, it is intended that all matter contained in this application, including all theoretical mechanisms and/or modes of interaction described above, shall be interpreted as illustrative only and not limiting in any way the scope of the appended claims.

The following examples are set forth as representative of the present invention. These examples are not to be construed as limiting the scope of the invention as these and other equivalent embodiments will be apparent in view of the present disclosure and appended claims.

EXAMPLE 1

The nanoaggregate (or nanocomposite) of nano calcium fluoride and amorphous calcium carbonate phosphate fluoride (ACCPF) was synthesized by mixing 8 mL of carbonate containing 1 mol/L tripotassium phosphate, 16 mL of 1 mol/L potassium fluoride and 13.3 mL of 1.5 mol/L calcium chloride. The precipitate was washed with 2% ammonia hydroxide, followed by ethanol, and then dried. The x-ray powder diffraction pattern in FIG. 1 shows that the calcium fluoride was poorly crystalline, with measured d spacing (Å) of 3.11, 1.92, and 1.64, together with a broad band of ACCPF with maximum around $2\theta=31$. The infrared spectrum in FIG. 2 shows the wavenumbers of amorphous bands of phosphate at 575 and 1050 and amorphous bands of carbonate at 1420 and 1490. FIG. 3 shows the characterization of this sample by Scanning Electron Microscopy.

EXAMPLE 2

A non-aqueous, rosin-based varnish contains 10 wt-% calcium sulfate (Plaster of Paris), 6 wt-% disodium phosphate, and 5 wt-% sodium fluoride and has a calculated F/Ca molar ratio of 1.7. Each of these calcium, phosphate, and fluoride salts is present in the varnish in the form of solid particles, having an average diameter of about 25 μm. When this varnish is applied to the surface of a tooth inside the mouth, the salts dissolve readily in aqueous saliva, resulting in sufficient concentrations of calcium, phosphate, and fluoride ions in the proper ratios for the precipitation of a calcium fluoride/ACPF nanocomposite. The composite then converts to fluoride-containing apatite, the tooth mineral.

COMPARATIVE EXAMPLE 2

Comparative data showed that the varnish composition of Example 2 provided 4 times more fluoride for tooth fluoridation and remineralization, and at a faster rate, relative to a control composition. This control composition contained 5 wt-% sodium fluoride, having the same average particle size and in the same varnish, as the composition of Example 2. However, the calcium and phosphate salts were not present in the control composition.

What is claimed is:

1. A composition for remineralizing a tooth comprising:
 (a) a calcium salt
 (b) a phosphate salt, and
 (c) a fluoride salt,
 wherein (a), (b), and (c) are water-soluble salts suspended in a non-aqueous carrier, wherein, when applied onto the tooth, said composition releases calcium, phosphate, and fluoride ions which form a nanoaggregate of calcium fluoride and an amorphous calcium phosphate-containing compound, wherein the nanoaggregate exhibits an x-ray powder diffraction pattern and an infrared spectrum characteristic of the calcium fluoride and the amorphous calcium phosphate-containing compound, respectively, wherein the released solution has a degree of supersaturation between 1.0 and 10.0 with respect to both calcium fluoride and amorphous calcium phosphate.

2. The composition of claim 1, wherein said calcium salt is selected from the group consisting of calcium sulfate, calcium oxide, calcium chloride, calcium nitrate, calcium acetate, calcium lactate, calcium glycerophosphate, and mixtures thereof.

3. The composition of claim 1, wherein said phosphate salt is selected from the group consisting of a sodium phosphate, a potassium phosphate, an ammonium phosphate, a calcium phosphate, and a peroxyphosphate.

4. The composition of claim 1, wherein said fluoride salt is selected from the group consisting of sodium fluoride, potassium fluoride, ammonium fluoride, sodium monofluorophosphate, sodium silicate hexafluoride, and calcium silicate hexafluoride.

5. The composition of claim 1, further comprising an antimicrobial agent which is incorporated into said nanoaggregate.

6. The composition of claim 5, wherein said antimicrobial agent is chlorhexidine.

7. The composition of claim 1, further comprising a whitening agent.

8. The composition of claim 7, wherein said whitening agent is a hexametaphosphate.

9. The composition of claim 7, wherein said whitening agent is a peroxide.

10. The composition of claim 9, wherein said whitening agent is carbamide peroxide.

11. A method for remineralizing a tooth with a nanoaggregate of calcium fluoride and an amorphous calcium phosphate-containing compound, the method comprising applying the composition of claim 1 to said tooth, either during or before the formation of said nanoaggregate.

12. The composition of claim 1, wherein calcium fluoride and amorphous calcium phosphate compound ionic products in the released solution both exceed their respective solubility products.

13. The composition of claim 1, wherein the non-aqueous carrier comprises a varnish, and the calcium, phosphate, and fluoride salts increase porosity of the varnish.

* * * * *